(12) United States Patent
Lilie et al.

(10) Patent No.: US 9,201,031 B2
(45) Date of Patent: Dec. 1, 2015

(54) CLOUD ICE DETECTOR

(75) Inventors: Lyle E. Lilie, Ashford, CT (US);
Christopher P. Sivo, Ellington, CT (US); Daniel B. Bouley, Stafford Springs, CT (US)

(73) Assignee: Science Engineering Associates, Inc., Mansfield Center, CT (US)

( * ) Notice: Subject to any disclaimer, the term of this patent is extended or adjusted under 35 U.S.C. 154(b) by 747 days.

(21) Appl. No.: 13/543,253

(22) Filed: Jul. 6, 2012

(65) Prior Publication Data

US 2014/0007654 A1 Jan. 9, 2014

(51) Int. Cl.
*G01N 25/04* (2006.01)

(52) U.S. Cl.
CPC ..................... *G01N 25/04* (2013.01)

(58) Field of Classification Search
CPC ........ B64D 15/20; B64D 15/12; B64D 15/22; B64D 15/00; B64D 15/14; G01W 1/02; F03D 11/0025; F03D 11/0091; G01N 25/04
USPC ................. 73/25.05, 170.26, 31.05
See application file for complete search history.

(56) References Cited

U.S. PATENT DOCUMENTS

| | | | |
|---|---|---|---|
| 3,873,927 A | 3/1975 | Overall | |
| 4,333,004 A | 6/1982 | Forgue et al. | |
| 5,686,841 A | 11/1997 | Stolarczyk et al. | |
| 5,710,408 A | 1/1998 | Jones | |
| 6,239,601 B1 | 5/2001 | Weinstein | |
| 6,377,207 B1 | 4/2002 | Solheim et al. | |
| 6,560,551 B1 | 5/2003 | Severson et al. | |
| 6,776,037 B2 | 8/2004 | Maatuk | |
| 6,847,903 B2 | 1/2005 | Severson et al. | |
| 7,643,941 B2 | 1/2010 | Lilie et al. | |
| 2005/0251341 A1 | 11/2005 | Nielsen | |
| 2005/0268710 A1 | 12/2005 | Rasmussen et al. | |
| 2010/0131203 A1* | 5/2010 | Lilie et al. ........................ | 702/3 |

OTHER PUBLICATIONS

Goldschmidt, V.W. et al., The Hot Wire Anemometer as an Aerosol Droplet Size Sampler, Press, 1969, vol. 3, pp. 643-651.

* cited by examiner

*Primary Examiner* — Daniel S Larkin
*Assistant Examiner* — Jamar Ray
(74) *Attorney, Agent, or Firm* — Carmody Torrance Sandak & Hennessey LLP

(57) ABSTRACT

A system for detecting the presence of ice crystals in a cloud comprising two thin walled semicylinder-shaped sensors, one having a concave inner surface and oriented longitudinally in a leading edge of an airfoil and the other having a convex outer surface being oriented longitudinally in the leading edge of the airfoil so that cloud water flows towards and into contact with the convex outer surface; a temperature controlling arrangement for heating the two sensors and maintaining them at a substantially constant temperature; and a comparison arrangement for finding a difference between (i) a power to maintain the temperature of the first sensor at its substantially constant temperature (ii) a power to maintain the temperature of the second sensor at its substantially constant temperature; and comparing the difference of the powers to a threshold value for evidencing the presence or predetermined amount of ice in the cloud water.

6 Claims, 10 Drawing Sheets

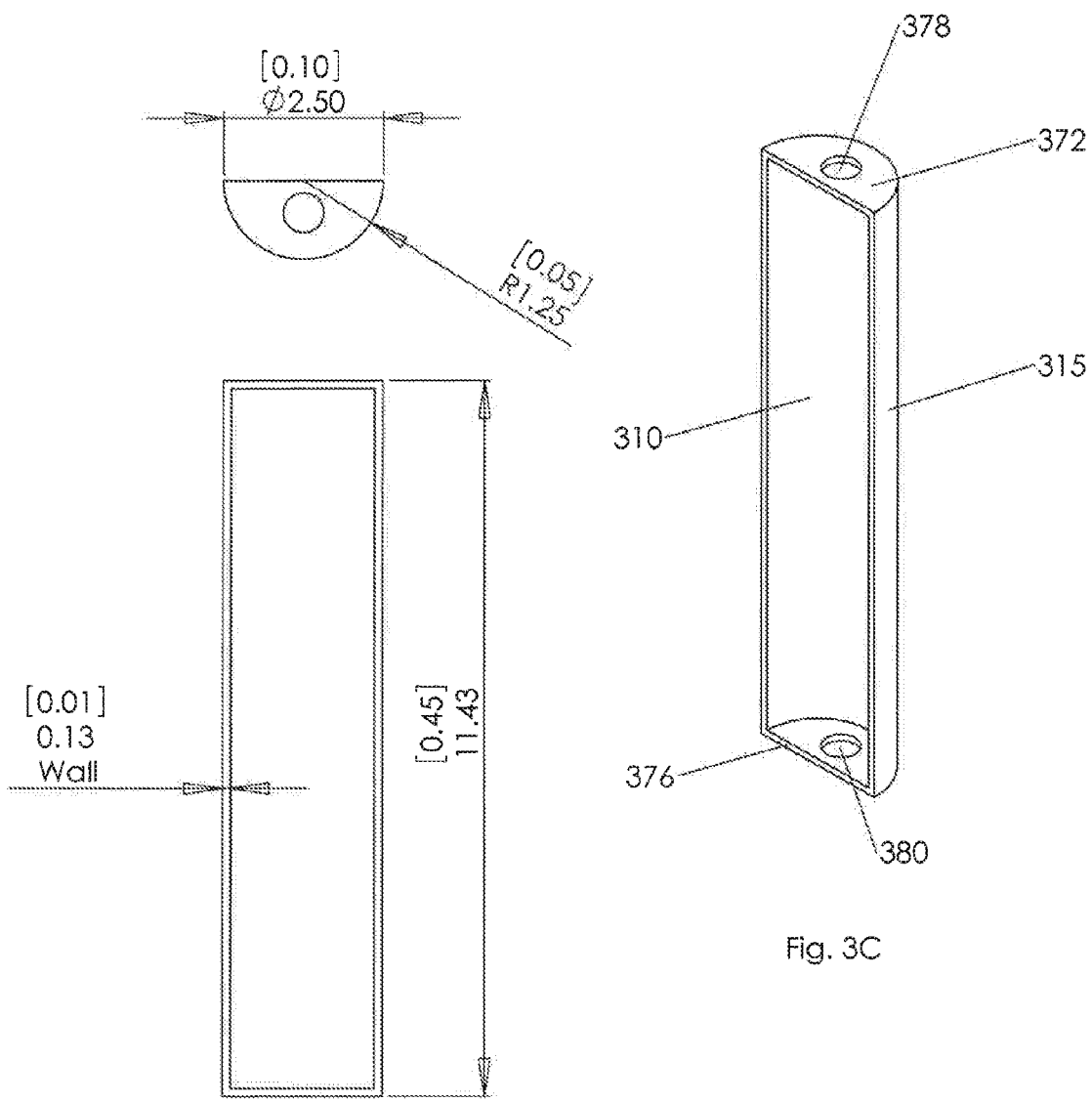

CLOUD ICE DETECTOR

FIELD OF THE INVENTION

The present invention is generally directed to cloud ice sensors, and in particular, to a system and methodology for providing, among other things as set forth herein, a measure of an amount of ice in a cloud containing liquid water, ice water or both.

BACKGROUND OF THE INVENTION

High concentrations of ice crystals have been identified as a hazard to jet aircraft engines and aircraft external sensors such as pitot (airspeed) probes. It was only in the last 5-10 years that enough previously unexplained engine and aircraft problems were collected together, studied and attributed to ice crystals.

Ice crystals are a major issue for general and commercial aviation, especially for large transport category aircraft because they operate at higher altitudes and consequently spend a greater proportion of their time operating in the presence of ice crystals. The icing problem for these aircraft has recently become more acute because of the tremendous growth in commercial aviation.

It is well known that the total water content in a cloud includes both unfrozen droplets (liquid water) and frozen water in the form of ice crystals. The ice water content (IWC) in the cloud can be determined by comparing the liquid water content (LWC) to the total water content (TWC). That is, IWC=TWC−LWC.

It is also known that one way to determine LWC alone, for example, is to use a heated sensor element that tends to "retain" liquid water but ignore ice crystals. Water "retained" by the sensor is continuously evaporated by a portion of the applied power. The total power used to evaporate the liquid water, after corrections for cooling from moving air alone, can provide a measure of liquid, water content.

Likewise, TWC is estimated by using a sensor that tends to retain both liquid water and ice crystals. The retained ice crystals (after being converted to water) and the liquid water "retained" by the sensor are both continuously evaporated by the applied power. The total power used to evaporate the net liquid water, after corrections for cooling from moving air alone, gives a measure of the total water content.

It is then a matter of performing the subtraction TWC (power)—LWC (power) to determine if the power difference associated with an amount of ice crystals equals or exceeds a predetermined amount.

A cloud water measurement system which uses a compensation sensor to account for the differences between dry air cooling of the cloud water sensors used is described in U.S. Pat. No. 7,643,941, the subject matter of which is incorporated by reference as if fully set forth herein.

However, further developments are believed achievable. For example, a robust device that provides a warning of the presence of threshold amounts of ice crystals using principles outlined herein and without the need for a separate sensor to compensate for cooling due moving air alone, is desirable and achievable by the invention disclosed herein.

SUMMARY AND OBJECTIVES OF THE INVENTION

It is thus an objective of the present invention to overcome the perceived deficiencies in the prior art.

Specifically, it is an objective of the present invention to provide an improved rugged sensor arrangement to monitor for the presence of ice crystals in a cloud.

Further objects and advantages of this invention will become more apparent from a consideration of the drawings and ensuing description.

The invention accordingly comprises the features of construction, combination of elements, arrangement of parts and sequence of steps which will be exemplified in the construction, illustration and description hereinafter set forth, and the scope of the invention will be indicated in the claims.

Therefore, to overcome the perceived deficiencies in the prior art and to achieve the objects and advantages set forth above and below, a preferred embodiment of the present invention is, generally speaking, directed to a system for detecting the presence of ice in a cloud as the system passes through the cloud.

In a first preferred embodiment, the system comprises a first thin walled semicylinder-shaped sensor, said first sensor having a concave inner surface and oriented longitudinally in a leading edge of an airfoil so that cloud water flows towards and into contact with the concave inner surface; a second thin walled semicylinder-shaped sensor, said second sensor having a convex outer surface and being at least substantially the same size as the first sensor, the second sensor further being oriented longitudinally in the leading edge of the airfoil so that cloud water flows towards and into contact with the convex outer surface; a temperature controlling arrangement for heating the first sensor and maintaining a temperature of the first sensor at a substantially constant temperature; and heating the second sensor and maintaining a temperature of the second sensor at a substantially constant temperature; and a comparison arrangement for finding a difference between (i) a power to maintain the temperature of the first sensor at its substantially constant temperature (ii) a power to maintain the temperature of the second sensor at its substantially constant temperature; and comparing the difference of the powers to a threshold value; whereby the difference evidences the presence of ice in the cloud water.

In a specific preferred embodiment, the temperature controlling arrangement comprises a first temperature controller for heating the first sensor and maintaining a temperature of the first sensor at a substantially constant temperature; and a second temperature controller for heating the second sensor and maintaining a temperature of the second sensor at a substantially constant temperature.

In another preferred embodiment, the present invention is directed to an aircraft based system for detecting a presence of ice crystals in a cloud as the system passes through the cloud that comprises a first heated sensor adapted for retaining ice water and liquid water during evaporation by a power applied to the first sensor by a first temperature controller having a first power output signal proportional to the power applied; a second heated sensor adapted to retain liquid water in the presence of ice water and liquid water during evaporation by a power applied to the second sensor by a second temperature controller having a second power output signal proportional to the power applied; said first and second sensors arranged in a leading edge of an airfoil so power needed to keep first and second sensors at a given temperature is substantially the same in the presence of moving dry air; and a comparator for receiving the first and second power output signals and outputting a difference signal to a threshold detector for determining whether the difference signal exceeds a threshold that indicates presence of ice crystals.

In yet another preferred embodiment, the present invention is directed to an aircraft based system for detecting a presence of ice crystals in cloud water as the aircraft passes through the cloud that comprises a first heated sensor located in a leading edge of an airfoil and adapted for retaining ice water and liquid water during evaporation by a measured power applied to the first sensor and having a first heat loss due to dry air; a second heated sensor located in the leading edge of the airfoil and adapted to retain liquid water in the presence of ice water and liquid water during evaporation by a measured power applied to the second sensor and having a heat loss due to dry air substantially equal to the first heat loss; and a comparator for receiving the measured powers output signals and outputting a difference signal that is fed to a threshold detector for determining whether the difference signal exceeds a threshold, whereby the exceeding of the threshold is an indication of the presence of ice crystals.

In yet another preferred embodiment, the present invention is directed to an aircraft based system for detecting a presence of ice crystals in cloud water as the aircraft passes through the cloud, wherein the system comprises a first self heated sensor adapted to respond to both ice water and liquid water and a second self heated sensor adapted to selectively respond to liquid water, said sensors mounted in a leading edge of an airfoil and further adapted so that heat lost from the first and second sensors are substantially the same as the sensors pass through dry air.

In each of the preferred embodiments, the present invention is mounted to an airplane, but other aircraft are contemplated by the present invention. Also, the present invention uses a standalone airfoil to house the sensing elements but it is contemplated that the detector could be built into an existing airfoil section already part of the airplane or its engines.

BRIEF DESCRIPTION OF THE DRAWINGS

The above set forth and other features of the invention are made more apparent in the ensuing Description of the Preferred Embodiments when read in conjunction with the attached Drawings, wherein:

FIGS. 3A, 3B and 3C (which also may collectively be referred to as "FIG. 3") are differing views of a basic sensor design used for the TWC and LWC sensors in accordance with a preferred embodiment of the present invention with the units being illustrated in millimeters (with inches being represented in the brackets);

Identical reference numerals in the figures are intended to indicate like parts, although not every feature in every figure may be called out with a reference numeral.

DETAILED DESCRIPTION OF THE PREFERRED EMBODIMENTS

The invention uses a number of important principles: the first is that heat loss due to evaporation from specific sensor geometry can be used in an analysis of cloud water to differentiate between water and ice. The geometry of the sensor is important since it affects its ability to "retain" and/or "hold" the water from a cloud long enough to cause evaporation. Another important principle is that the total electrical power required to maintain a heated sensing element at a preset and approximately constant temperature is substantially equal to the power lost due to interaction of the sensing element with the cloud environment.

It is known that the total power input to a LWC sensor to hold the temperature of the sensor at a fixed predetermined value when it is moving relative to moisture laden air is primarily made up of two components; the power to keep the sensor at the temperature as if the air was dry and the power needed to evaporate the moisture in the air.

Prior art systems have used compensation sensors that are configured to respond to only the cooling effects of dry air to isolate the power needed to evaporate the moisture alone in air. Advantageously, use of a separate compensation sensor is not necessary with the present invention.

That is, the present inventors have discovered that two substantially identical self heated thin wall semi-cylinder shaped sensors, when mounted in a leading edge of an airfoil, can be used to identify the presence of ice water without a need for compensation sensors. This surprising result emanates from their orientation and positioning in the airfoil and the fact that the cooling effects of dry air are the same for both sensors even though they are rotated 180 degrees relative to each other. Also possibly influencing this result is the detected airflow patterns in the vicinity of the leading edge and over the airfoil.

Figure 1:
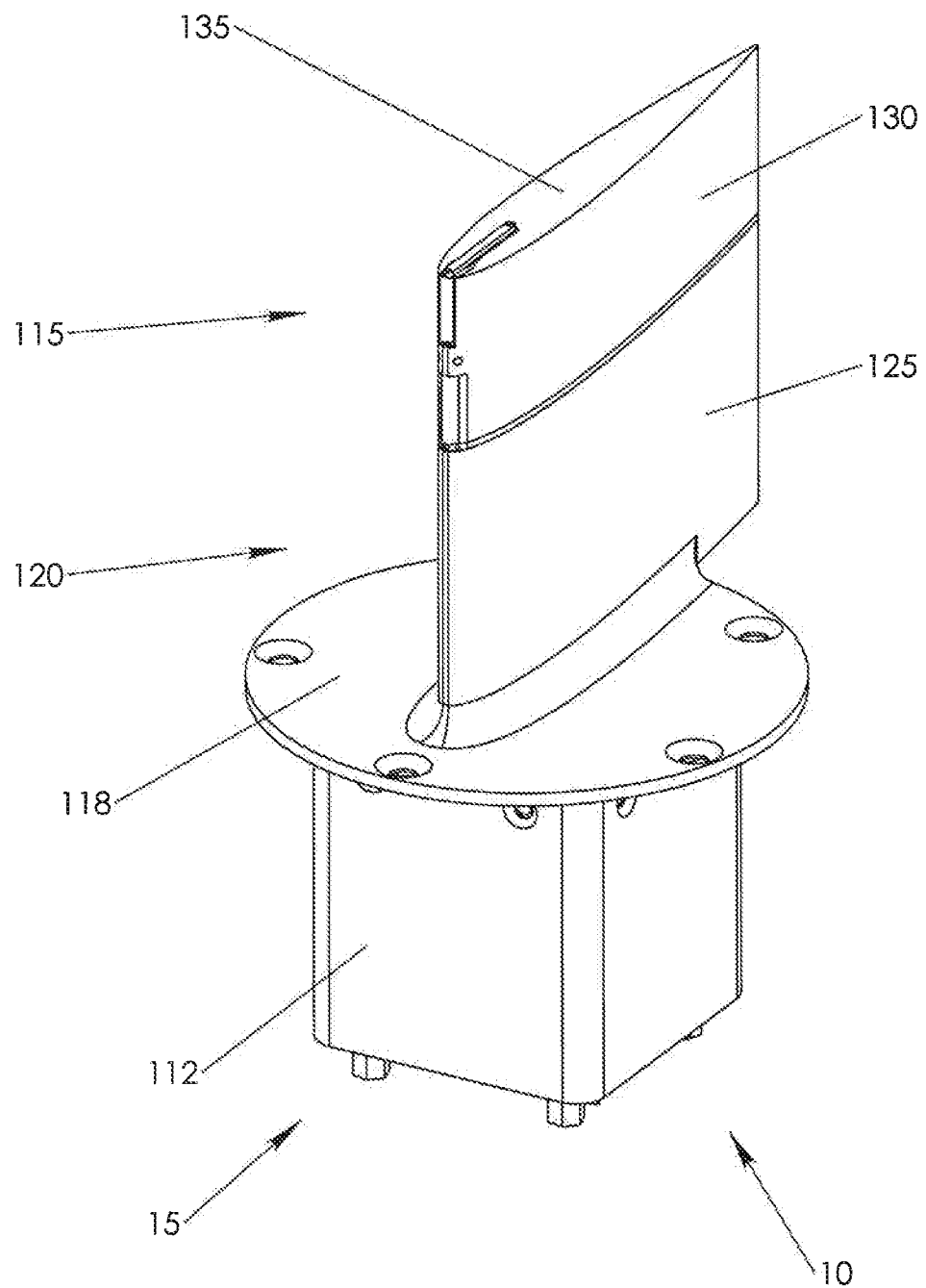
FIG. 1 is a view of an overall cloud ice detector system constructed in accordance with a preferred embodiment of the present invention.
Figure 2:
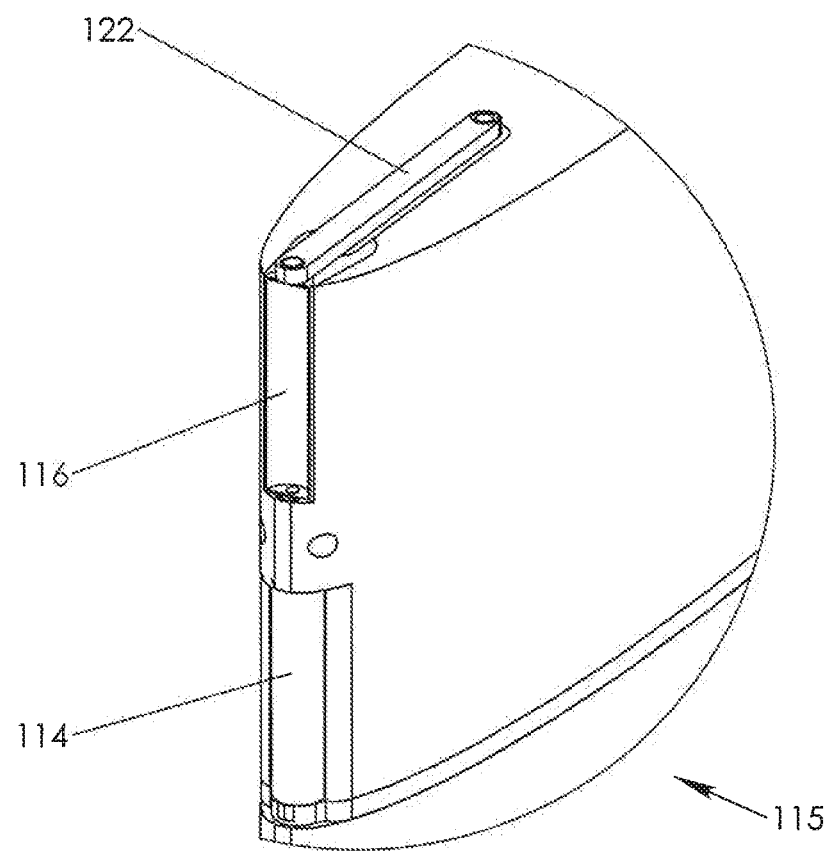
FIG. 2 is a section of the airfoil of FIG. 1.

The sensors are shown generally at 115 in FIG. 1 and specifically in FIG. 2 as TWC sensor 116 and LWC sensor 114. FIG. 2 shows an enlarged section of FIG. 1 to more particularly illustrate a preferred relative orientation of LWC sensor 114 and TWC sensor 116. FIG. 2 further shows TWC sensor 116 and LWC sensor 114 within an airfoil section further disclosed below. FIG. 2 is illustrative of sensors 116 and 114 being mounted in a leading edge of an airfoil of a wing of an aircraft, but this is by example and not limitation. For example, sensors 116 and 114 may be mounted in a leading edge of an airfoil like component of any engine assembly.

TWC sensor 116 is oriented so that the direction of an airstream is towards and into its concave surface and therefore tends to act like a total water content (TWC) sensor in that it responds to the presence of both liquid water and ice crystals. Semi-cylindrical shaped LWC sensor 114 is rotated 180 degrees (about its longitudinal axis) relative to TWC sensor 116 so that the direction of an airstream is towards and onto the convex cylinder outer surface of LWC sensor 114 and thus tends to be more sensitive to liquid water and insensitive to ice crystals and hence acts similar to a liquid water sensor.

The ice crystal detector system of the present invention uses the difference in heat loss from TWC sensor 116 and LWC sensor 114 to determine the presence of and/or a predetermined amount of ice crystals. More specifically, for a given cloud airstream, the preferred embodiments disclosed herein determine the difference between the heat lost to evaporate, an amount of total water (ice water plus liquid water) and the heat lost to evaporate only liquid water to then generate a measure of the heat lost to evaporate the ice crystals alone. This measure is then compared against one or more predetermined thresholds to determine if a particular ice crystal content (e.g. in gm/m$^3$) is present or has been exceeded. These thresholds are determined using for example FIG. 5c which shows a power threshold of approximately 1.8 watt difference for ice crystals of 0.2 gm/m3 at an airspeed of 250 knots. At airspeeds other than the 250 knots referenced, the threshold, in terms of gm/m3, increases or decreases linearly with decreasing or increasing airspeed. As the airspeed increases, the power threshold represents a smaller amount of ice crystals per unit of volume, making the detector more sensitive with increasing airspeed which fits well with the typical (higher) airspeeds where problems with ice crystal ingestion have been found.

It is important to note that a primary concern for aircraft safety is the amount of ice crystals being intercepted by the aircraft per unit time, which also changes linearly with airspeed. In simplified form, ingestion rate equals interception area times airspeed times ice crystal concentration (gm/m3). Ice crystal concentration is proportional to detector power difference divided by airspeed. Therefore, ingestion rate is directly proportional to the TWC IWC power difference, so a fixed power threshold represents a fixed ingestion rate threshold.

More specifically, reference is again made to FIG. 1, which illustrates a cloud ice detector system in accordance with a preferred embodiment of the present invention, generally indicated at 10. System 10 includes an ice detector 15 and an aircrew display (not shown) preferably configured to receive a signal to indicate the presence of ice crystals. In one embodiment, the signal is in the form of a logic level which is signaled to an aircrew display as part of a digital word in an ARINC communications channel. Alternative embodiments include those where the logic level or a switch closure for example is hard wired to the aircrew display. And in still yet another embodiment, the signal could be sent directly to the engine control system or to other flight computers in the aircraft without necessarily alerting the flightcrew.

Ice detector 15 includes a preferably symmetrical airfoil 120 having a NACA 0021 cross-section 135. Airfoil 120 further includes airfoils sections 125 and 130, with LWC sensor 114 and TWC sensor 116 generally and preferably located at a front edge of section 130. Ice detector 15 also preferably includes an airframe interface flange 118 and an electronics compartment 112. Ice crystal detector 15 is preferably mounted so that the airfoil section 120 is oriented in a vertical direction or a horizontal direction.

Figure 6:
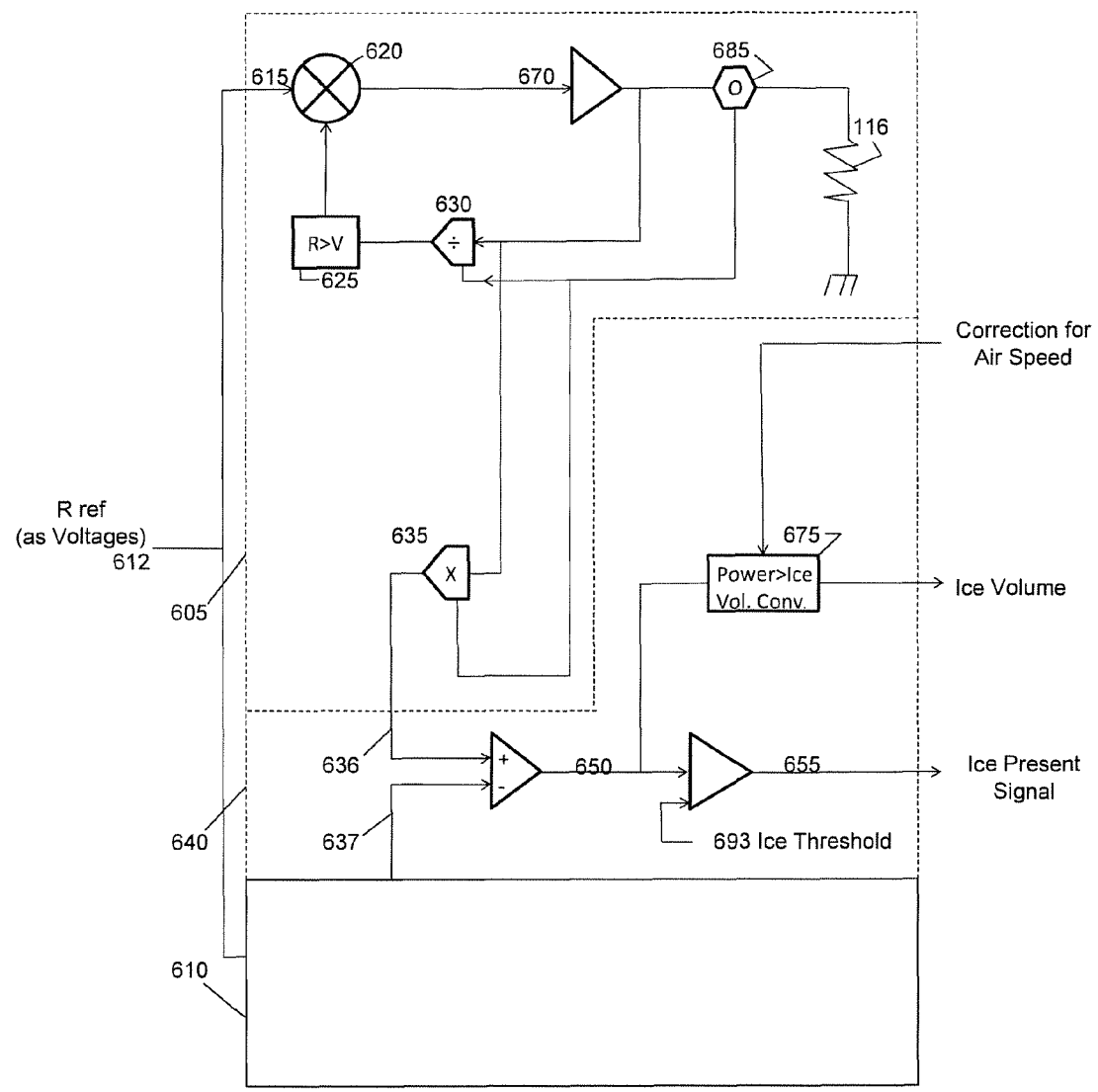
FIG. 6 is an exemplary temperature control circuit constructed in accordance with the present invention for powering the LWC and TWC sensors of the present invention.
Figure 7:
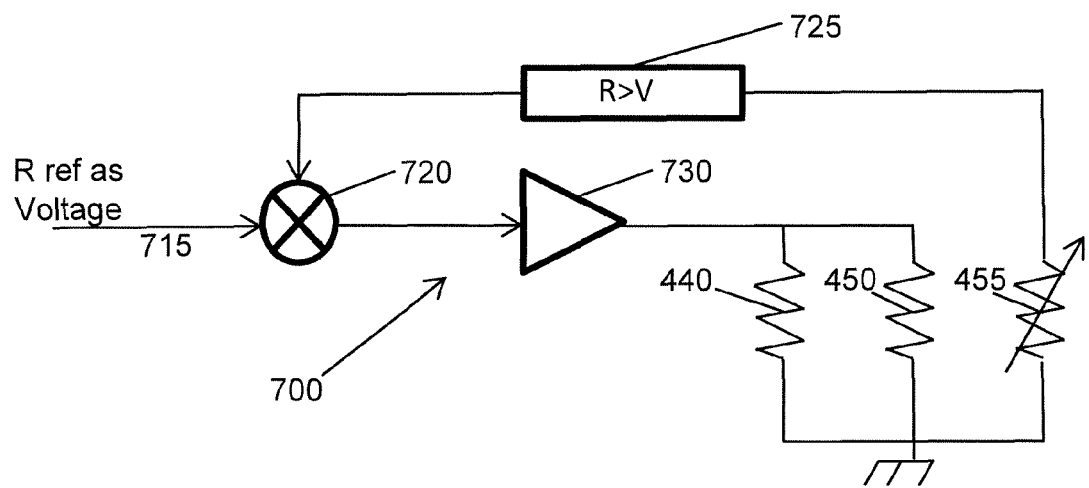
FIG. 7 is a block diagram of an airfoil deice temperature control circuit constructed in accordance with a preferred embodiment of the present invention.

In a preferred embodiment, electronics compartment 112 includes individual temperature controllers 605 and 610 (see FIG. 6) and a deice temperature control system 700, shown generally in FIG. 7. Temperature controller 605 preferably keeps TWC sensor 116 at a predetermined temperature and temperature controller 610 preferably keeps LWC sensor 114 at a predetermined temperature, both of which are preferably about 140 degrees C. The temperature of each sensor 114, 116 is maintained by tracking each sensor's respective electrical resistance and holding that resistance substantially constant by varying the amount of electrical power applied to each of sensors 114, 116. The magnitude of the difference in power applied to LWC sensor 114 and TWC sensor 116 is an indicator of the presence of ice crystals. Power to ice detector 15 is provided through connector 460 while an output signal is provided via connector 465.

In a preferred embodiment, temperature controllers 605, 610 may receive power from the aircraft power supply.

Deice temperature control system 700 includes individual heaters 440 and 450 (see FIG. 4) for reducing the possibility of airfoil 120 icing and reducing heat lost from the LWC sensor 114 and TWC sensor 116 to the surrounding structure. The temperature of airfoil 120 is sensed by thermistor 455 (see FIGS. 4, 7) to feed back a resistance value from which temperature is readily determined and controlled.

Preferred front, top (cross-sectional) and side (cross-sectional) views of LWC sensor 114 and TWC sensor 116 are shown in FIGS. 3A, 3B and 3C respectively. Preferably, each sensor has the same planar area projection facing into the direction of airflow of approximately 0.04 square inches, which is approximately the product of each sensor's respective width and height shown in FIG. 3. As also can be seen and discussed above, TWC sensor 116 and LWC sensor 114 are preferably substantially identical but are oriented differently relative to airfoil section 130 and the normal direction of airflow over the airfoil section. That is, in a preferred embodiment, the concave surface 310 (see FIG. 3C) of TWC sensor 116 is seen when looking into the leading edge of airfoil 120 from a position normal to the leading edge of airfoil 120. In comparison, the convex surface 315 (see FIG. 3C) of LWC sensor 114 is seen when looking into the leading edge of airfoil 120, all as shown in FIG. 2.

Figure 4A:
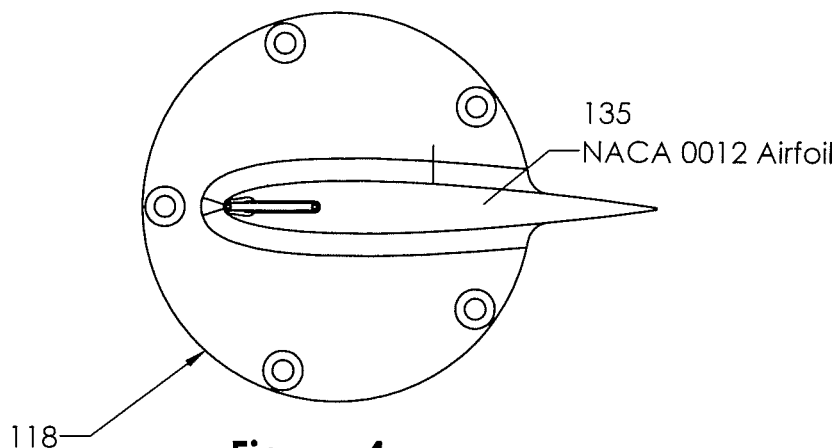
FIG. 4A shows a top view of the cloud ice detector and FIG. 4B shows a cross-section through the airfoil of FIG. 1 (collectively referred to herein as FIG. 4)
Figure 4B:
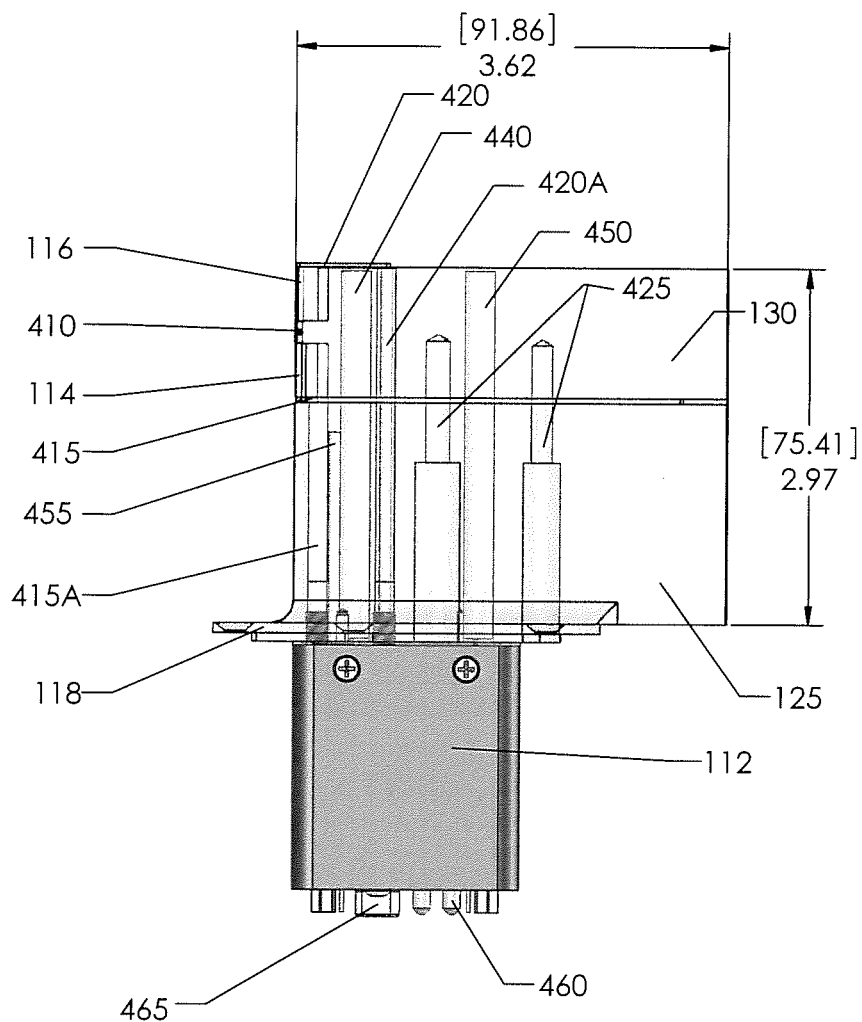

Referring to FIGS. 3 and 4, TWC sensor 116 and LWC sensor 114 include end caps 372 and 376 which are welded at each of the respective first and second ends of the semi-cylinders. End cap 372 of TWC sensor 116 includes connection hole 378 for receiving TWC signal strap 420. Signal strap 420 connects to signal strap extension 420A which then connects to temperature controller 605 (shown in FIG. 6) and mounted in electronics compartment 112.

Similarly, end cap 376 of LWC sensor 114 includes connection hole 380 for receiving LWC signal strap 415 which then connects to LWC signal strap extension 415A. LWC signal strap extension 415A then connects to temperature controller 610 (see FIG. 6), which is also mounted in the electronics compartment 112.

Connection hole 380 of sensor 116 and connection hole 378 are connected to common ground point 410 in FIG. 4.

Bolts 425 fasten together sections 125 and 130 of airfoil 120.

Surface roughness may be added to surface 310 of TWC sensor 116 and/or surface 315 of LWC sensor 114 in the form of ridges, convolutions and/or indentations, which tend to increase the retention of water and therefore give more opportunity for evaporation. Alternatively, bonding to the respective surface(s) a rough material having a high electrical resistance and low thermal resistance, such as diamond chips or silicon carbine chips, may be used to increase the surface roughness. Testing indicates that a surface roughness of greater than about approximately 2.5/j.m. peak to peak is preferred.

Testing for the sensor arrangement and airfoil design as illustrated in FIG. 1 was conducted in a wind tunnel and the results are shown in FIGS. 5A-5D. In particular, FIGS. 5A-5D depict the TWC element power on the vertical axis and the LWC element power on the horizontal axis. Similar tests were performed with the positions of the LWC sensor 114 and the TWC sensor 116 reversed in airfoil 120, yielding similar results.

Figure 5A:
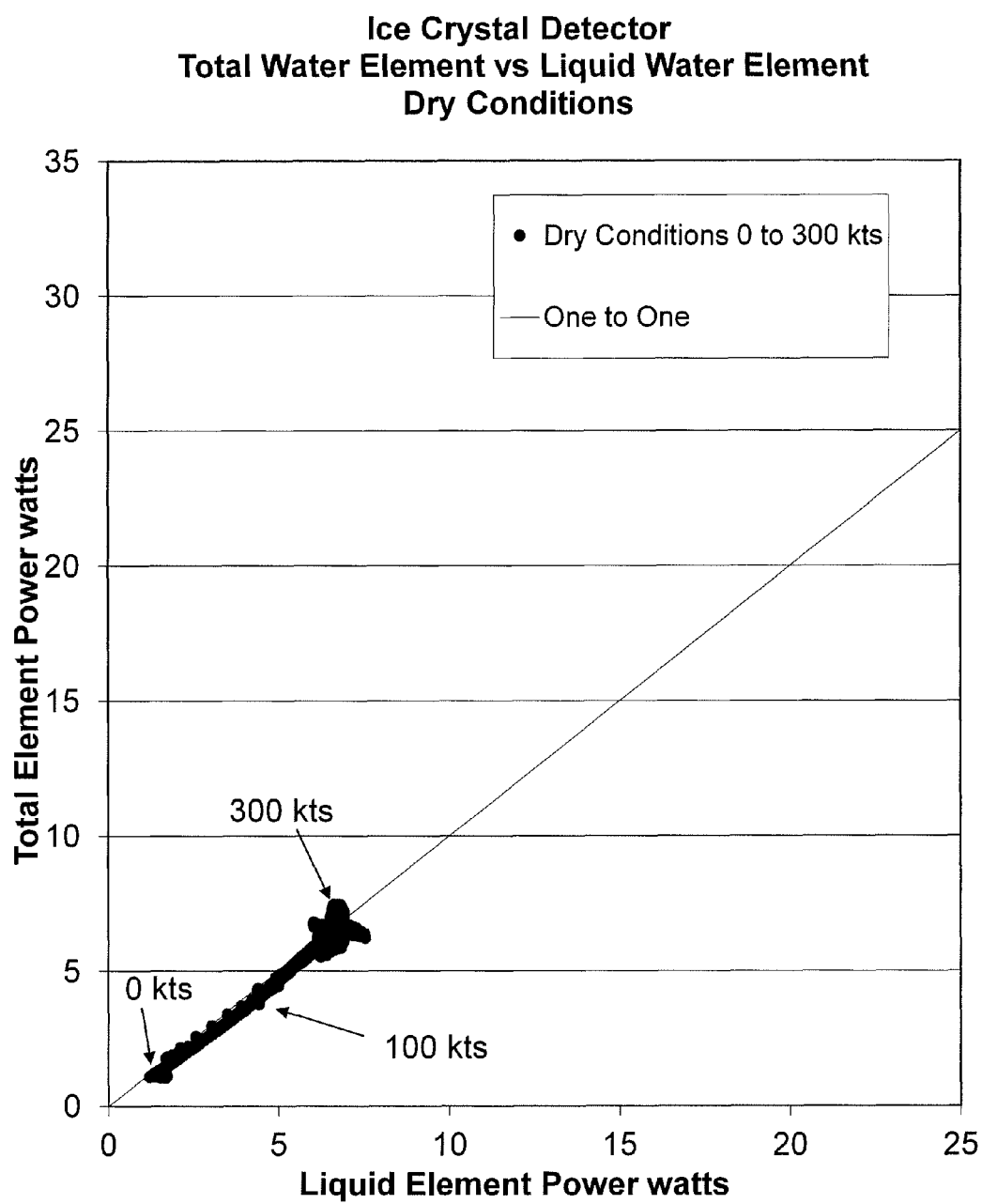
FIGS. 5A, 5B, 5C and 5D show wind tunnel test results for a preferred sensor arrangement of the present invention.

FIG. 5A shows that the cooling effects of dry air on TWC sensor 116 and on LWC sensor 114 in the preferred embodiment is the same from approximately zero (0) knots up to at least 300 knots. Said another way, there is a one to one correspondence between the heat lost from a TWC sensor, such as TWC sensor 116, and the heat lost from a LWC sensor, such as LWC sensor 114, in the presence of a stream of dry air. Importantly, this test confirmed that a sensor to compensate for cooling effects of dry air was not needed.

Figure 5B:
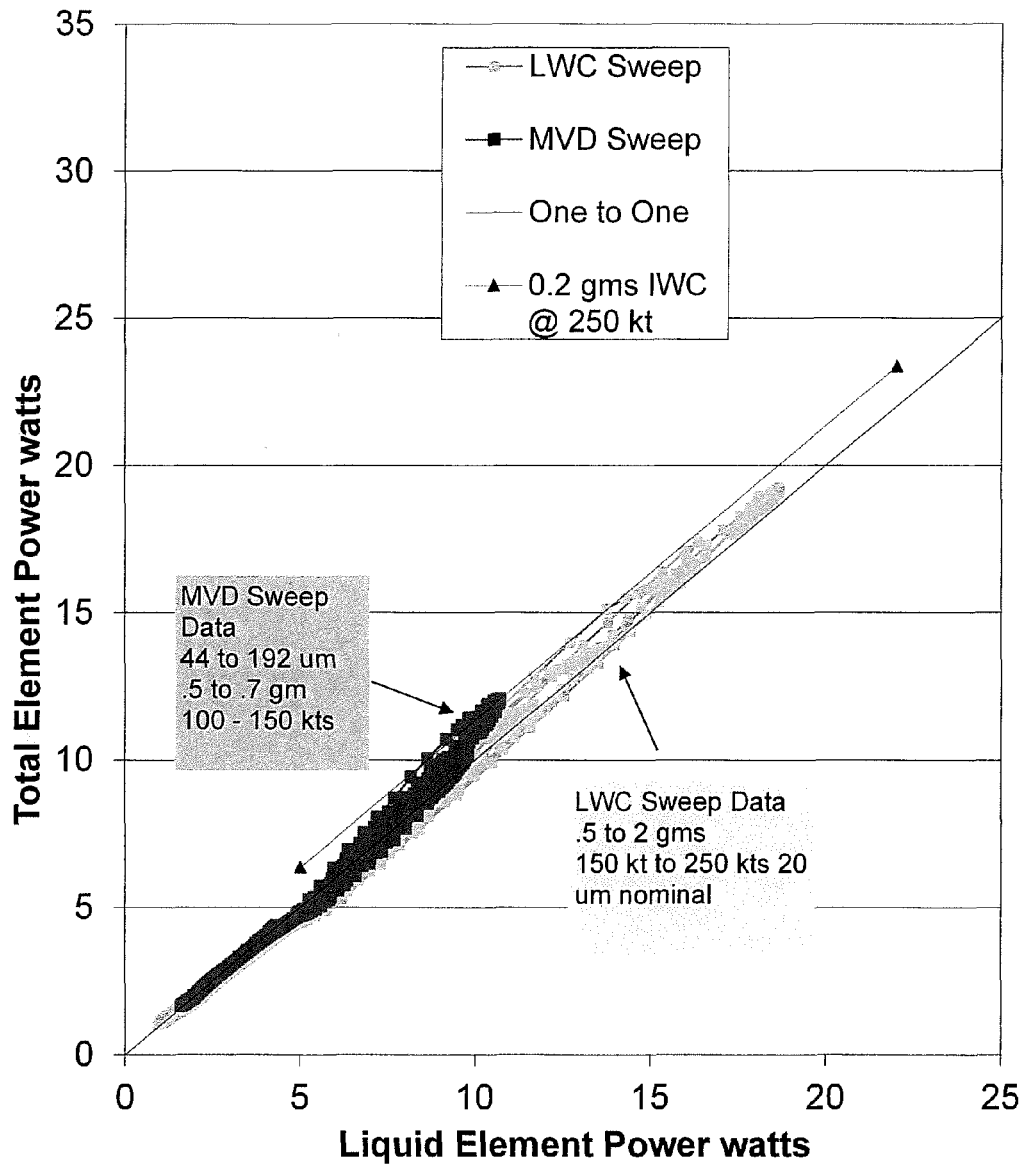

FIG. 5B illustrates the detector response over varying LWC and MVD conditions, and graphs TWC sensor power vs. LWC sensor power under different water droplet sizes and airspeeds and in the absence of ice crystals. Specifically, FIG.

5B illustrates that there is a substantially maximum difference of less than 1.8 watts between the power dissipated in TWC sensor 116 and the power dissipated in LWC sensor 114, and furthermore, the maximum difference is relatively independent of variations in droplet size and airspeed. This implies that any additional difference between the power dissipated by the TWC sensor compared to the LWC sensor can be attributed to the presence of ice crystals. Given that exposed area of the TWC sensing element is known, this power difference can, if the airspeed is known, be converted to an equivalent concentration of ice crystals. For FIG. 5B 1.8 watts of power difference is equivalent to 0.2 grams/m3 at an airspeed of 250 kts.

Figure 5C:
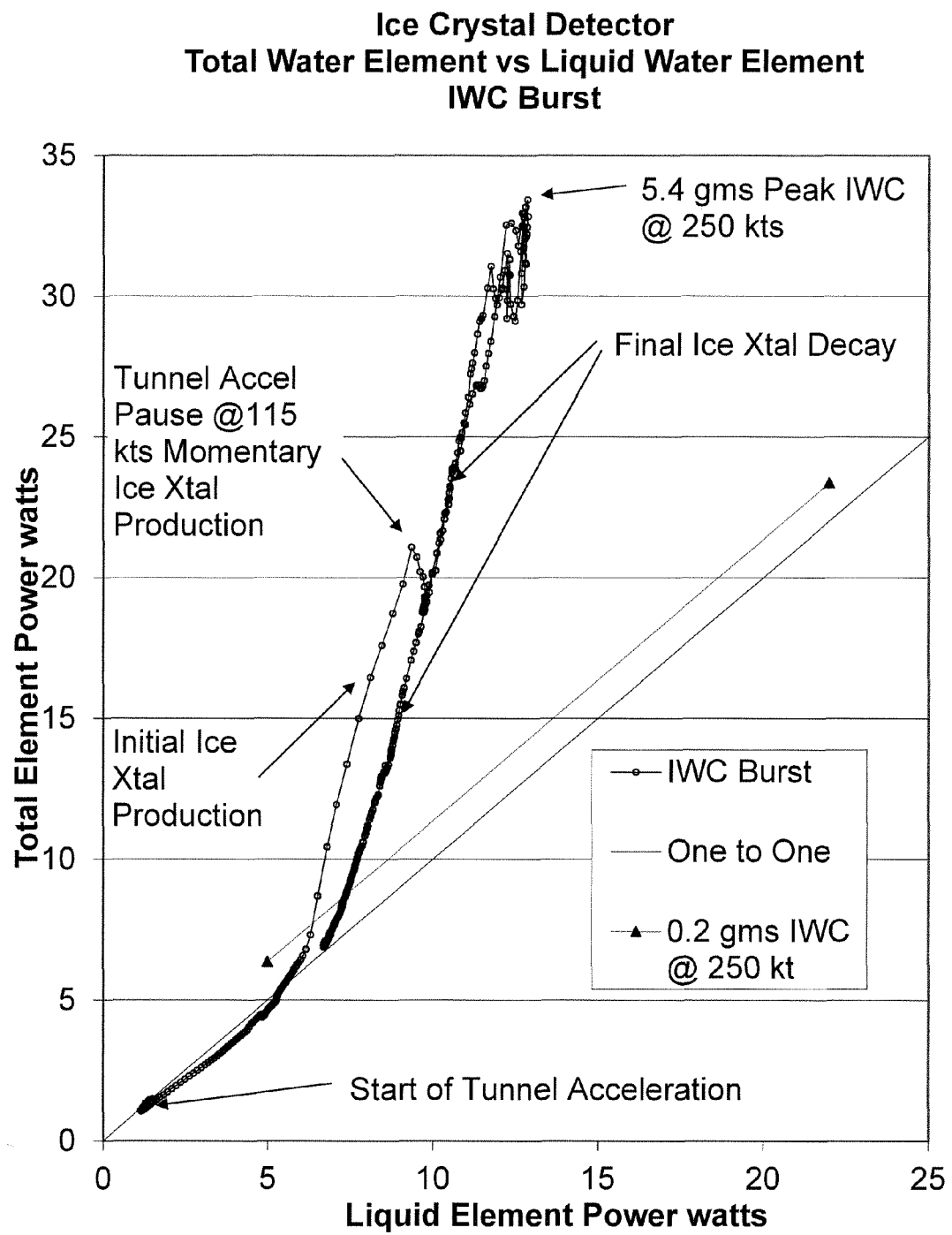

FIG. 5C shows the increase in the element power difference due ice crystals in the tunnel airflow. In this graph only ice crystals are introduced into the test chamber. The test procedure begins by running the tunnel at a set of conditions where ice crystals form and are deposited on the heat exchanger in the closed loop of the tunnel. This procedure is done prior to the actual test. The tunnel is then restarted and brought back up to speed. At some velocity during the tunnel acceleration, the accumulated ice crystals start to break free and pass into the test section where the detector is located. Eventually the number of ice crystals released per unit time peaks and then declines until the supply of crystals is exhausted. In this particular case the concentration of ice crystals peaked at 5.4 grams/m3 when the tunnel speed was approximately 250 knots.

Figure 5D:
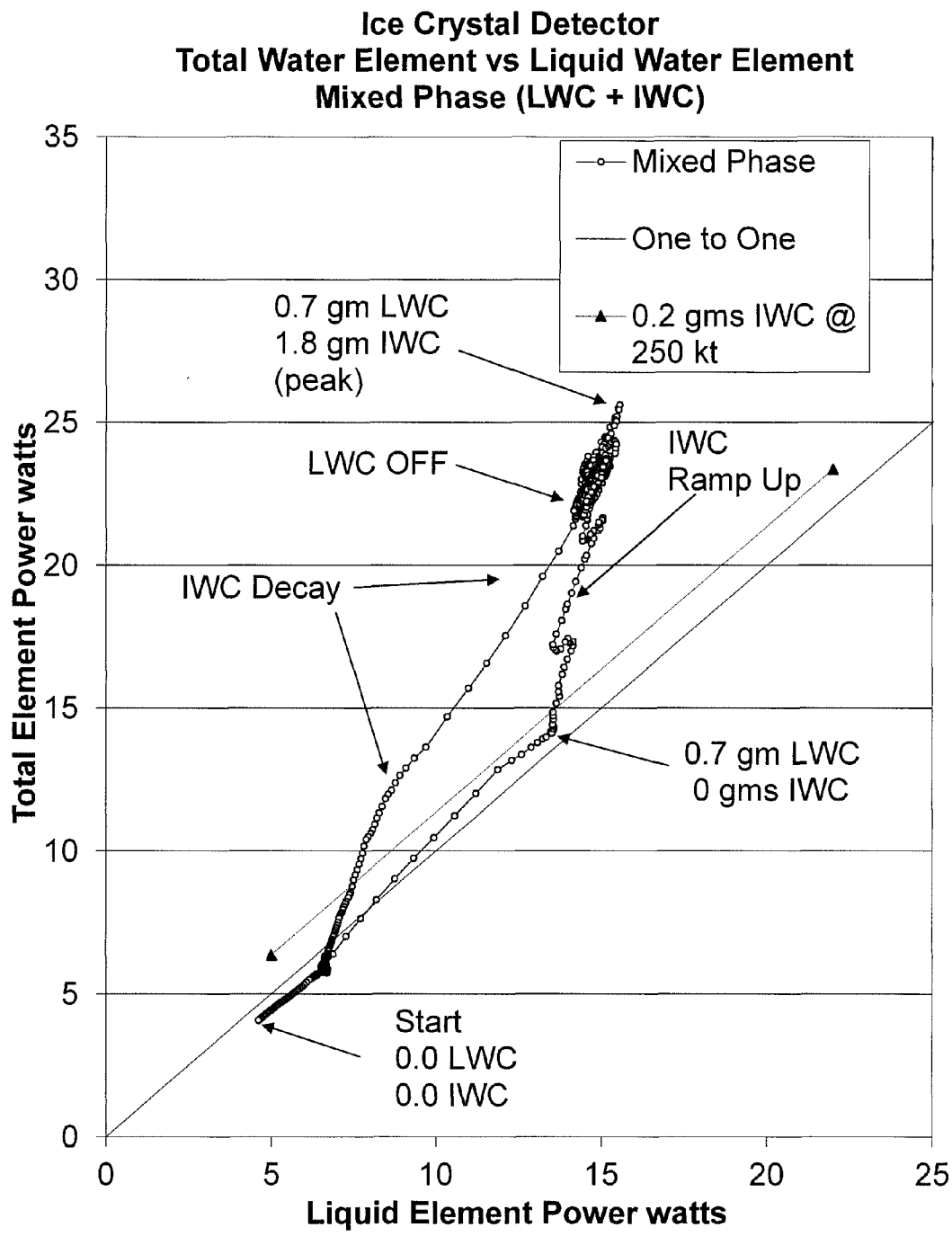

FIG. 5D shows TWC element power vs. LWC element power under mixed phase conditions, e.g. where ice crystals and liquid water are both present. At the test start there is no LWC or IWC in the airflow fed to the test chamber. The LWC of the airstream in the chamber is increased with time until it reaches 0.7 grams/m3 and ice crystals start to form from the liquid water spray. This is accomplished by setting the tunnel's spray parameters and the tunnel temperature to a specific setting were ice crystals form directly from the liquid spray. In the tunnel community, this is informally known as nozzle freeze out. Ice crystals continue to form and reach 1.8 grams/m$^3$, while the liquid water continues to circulate at LWC of 0.7 grams/m$^3$. Importantly the power dissipated in the TWC sensor has a rapid rate of rise as the IWC increase but the LWC stays substantially constant.

When the IWC reaches about 1.8 grams the liquid in the airstream to the tunnel was turned off so that the amount of water available to form crystals is reduced. The total amount of ice crystals begins to fall because the existing crystals fall to the ground and no ice crystals are being produced to replace those that fall out of the airstream.

Temperature Control Systems

The present invention provides three temperature controllers, namely controllers 605 and 610 of FIG. 6 and controller 700 of FIG. 7. Controllers 605 and 610 are substantially identical and are respectively used to control the temperature of TWC sensor 116 and LWC sensor 114, and as noted above, preferably control the power to respectively keep TWC sensor 116 and LWC sensor 114 at 140 C.

Determination of the total water content, the liquid water content and then ultimately the ice water content utilizes the principles that the power necessary to keep a self heated sensor at a fixed temperature is related to the moisture in the air passing over the sensor. That is, if a fixed power level was applied to LWC sensor 114 or TWC sensor 116, an increasing moisture level in the air flowing in contact with the sensor will tend to lower the temperature of the sensor while a decreasing amount moisture will tend to cause the temperature of the sensor to rise.

Therefore, if the temperature of one of the sensors, e.g. sensor 116 or sensor 114, was held constant for a varying amount of moisture in the air, the changes in power level to keep the temperature of the respective sensor constant is indicative of the changes in moisture in the air. The present invention utilizes the change in sensor resistance to indicate changes in sensor temperature; a lower sensor temperature will be indicated by a decreasing resistance R of the sensor while an increasing sensor temperature is indicated by an increasing R.

Stored values that characterize a temperature—resistance relationship of sensors 114 and 116 are characterized by two values, R@100° C. and dT/dR. The value R@100° C. gives sensor resistance in milliohms at 100° C. while the value dT/dR gives the slope of the temperature vs. resistance line in terms of degrees C. per milliohm. In the preferred embodiment, the stored values of R@100° C., dT/dR, are respectively 20 milliohms and 42° C./milliohm.

The operation of control system 600 will be explained with the aid of FIG. 6.

A voltage representing a desired resistance set point representing 140° C. is fed to error detector 620 at 615. The second input to error detector 620 is from R to V (resistance to voltage) converter 625 and is a voltage that represents the resistance of TWC sensor 116. This voltage value is based on the output of divider 630 which is the voltage across TWC sensor 116 divided by the current through TWC sensor 116 as measured by current sensor 685.

Controller 605 calculates the power delivered to TWC sensor 116 by multiplying the sensor voltage and current in multiplier 625. This power value is outputted at 636 from block 605. The output from error detector 620 is fed to PWM power amplifier 670 whose output preferably ranges between substantially zero (0) volts up to substantially three (3) volts, PWM power amplifier 670 is preferably based on a pulse width modulator.

In a similar manner, controller 610 controls the temperature of LWC sensor 114 and outputs a signal at 637 that is proportional to the power to LWC sensor 114.

In block 640, the difference between the power delivered to LWC sensor 114 (at line 637) and to TWC sensor 116 (at line 636) is determined in difference amplifier 650 and then are compared in threshold detector 655 to a power value at line 693 that represents a threshold value of ice crystals in a cloud. A logic level indicating that the threshold was exceeded can then be audibly and/or visually sent to the aircrew, such as via a visual display in the cockpit. In a preferred embodiment, this threshold can be set at the time of plane manufacture but in alternative embodiments, the threshold value(s) can be adjusted in flight.

In a further embodiment, the output of amplifier 650 may be sent to a correction block 675 wherein compensation signals, including at least airspeed and optionally altitude and temperature, are provided. The output of block 675 may then represent an actual volume of ice crystals present in cloud water, the value of which can be then sent audibly and/or visually to the crew in the cockpit.

Signal 637 is a measure of the heat loss per unit time for LWC sensor 114 as it experiences liquid water while signal 636 is a measure of the heat loss per unit time for TWC sensor 116 as it experiences liquid water, ice water or both.

Temperature control system 700 of FIG. 7 controls the average temperature of the airfoil in the vicinity of the TWC and LWC sensors. A preferred location of the temperature sensor (i.e. thermistor 455) and heaters 440 and 450 for airfoil 120 are shown in FIG. 4. Heaters 440 and 450 are preferably connected in parallel and fed by a power amplifier 730. Power amplifier 730 is preferably a pulse width modulator having a fixed frequency of approximately 895 Hz. The temperature of the airfoil 120 in the region of thermistor 455 is controlled by feeding back the resistance read at thermistor 455, converting the resistance value into a voltage and adjusting the output of power amplifier 730 to maintain thermistor 455 at a substantially constant temperature of preferably 50° C.

One end of thermistor 455 is connected to airfoil 120 which is at ground potential and the other end is connected to a resistance to voltage converter 725. The output of converter 725 is compared to a voltage (from line 715) representing the target resistance of thermistor 455 at 50° C. The difference between the reference voltage representing resistance of the thermistor 455 and a value at 50° C. is amplified by power amplifier 730 to adjust the output of power amplifier 730 and therefore attempts to reduce the error signal from block 720 closer to zero.

At low or zero airspeed, a minimum amount of deice power is required. As the airspeed increases or the ambient temperature decreases, the amount of deicing power will increase. Furthermore during encounters with liquid water and or ice water, extra power will be delivered by the deice control loop to compensate for the increased cooling of the impinging water. Preferably up to about 375 watts of heating power will be provided to airfoil 120 by heaters 440 and 450.

As will be understood by one skilled in the art, the electronic block diagrams provided herein may be implemented with hardware, software, firmware or a combination thereof. Likewise the hardware, software or firmware may be implemented using microprocessors, microcontrollers, programmable logic or analog or digital circuits. Power amplifiers are preferable constructed using pulse width modulation techniques but may also be constructed using analog circuits.

It will thus be seen that the objects set forth above, among those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It should also be understood that the following claims are intended to cover all of the generic and specific features of the invention described herein and all statements of the scope of the invention that as a matter of language might fall therebetween.

What is claimed is:

1. A system for detecting the presence of ice in a cloud as the system passes through the cloud, the system comprising:
    a first thin walled semicylinder-shaped sensor, said first sensor having a concave inner surface and oriented longitudinally in a leading edge of an airfoil so that cloud water flows towards and into contact with the concave inner surface;
    a second thin walled semicylinder-shaped sensor, said second sensor having a convex outer surface and being at least substantially the same size as the first sensor, the second sensor further being oriented longitudinally in the leading edge of the airfoil so that cloud water flows towards and into contact with the convex outer surface;
    a temperature controlling arrangement for:
        heating the first sensor and maintaining a temperature of the first sensor at a substantially constant temperature; and
        heating the second sensor and maintaining a temperature of the second sensor at a substantially constant temperature; and
    a comparison arrangement for:
        finding a difference between (i) a power to maintain the temperature of the first sensor at its substantially constant temperature (ii) a power to maintain the temperature of the second sensor at its substantially constant temperature; and
        comparing the difference of the powers to a threshold value;
    whereby the difference evidences at least one of a presence of and a predetermined amount of ice in the cloud water.

2. The system as claimed in claim 1, wherein the temperature controlling arrangement comprises:
    a first temperature controller for:
        heating the first sensor and maintaining a temperature of the first sensor at a substantially constant temperature; and
    a second temperature controller for:
        heating the second sensor and maintaining a temperature of the second sensor at a substantially constant temperature.

3. The system as claimed in claim 1, wherein the heating of the first sensor and maintaining a temperature of the first sensor at a substantially constant temperature uses a resistance of the first sensor as a measure of temperature of the first sensor.

4. The system as claimed in claim 1, wherein the heating of the second sensor and maintaining a temperature of the second sensor at a substantially constant temperature uses a resistance of the second sensor as a measure of temperature of the second sensor.

5. The system as claimed in claim 1, wherein the airfoil is a standalone airfoil and the first and second sensors are not mounted in a leading edge of an airfoil of a wing of an aircraft.

6. The system as claimed in claim 1, wherein the first and second sensors are mounted in a leading edge of an airfoil of a wing of an aircraft.

* * * * *